United States Patent [19]

Maxim et al.

[11] Patent Number: 5,702,128
[45] Date of Patent: Dec. 30, 1997

[54] RADIOGRAPHIC MARKER SYSTEM AND METHOD OF MAKING SAME

[75] Inventors: Rosemary S. Maxim, Farmington; Hermann K. Kasper, Plantsville, both of Conn.

[73] Assignee: Beekley Corporation, Bristol, Conn.

[21] Appl. No.: 683,175

[22] Filed: Jul. 18, 1996

[51] Int. Cl.⁶ .................................................. B42D 15/00
[52] U.S. Cl. ............................ 283/81; 283/100; 283/101
[58] Field of Search .............................. 283/81, 100, 101; 40/299, 630, 594; 206/820, 460; 428/40.1, 41.7, 41.8, 42.1, 42.2, 192, 194; D24/189; 156/268, 256; 378/162; 602/54, 57, 78

[56] References Cited

U.S. PATENT DOCUMENTS

| | | | |
|---|---|---|---|
| D. 364,922 | 12/1995 | Bierman | D24/189 |
| D. 372,787 | 8/1996 | Dozier et al. | D24/189 |
| 1,168,177 | 1/1916 | de Yoanna. | |
| 2,462,018 | 2/1949 | Wood. | |
| 3,068,863 | 12/1962 | Bowman. | |
| 3,078,183 | 2/1963 | Karalus. | |
| 3,171,959 | 3/1965 | Kozek et al.. | |
| 3,267,623 | 8/1966 | Block. | |
| 3,371,400 | 3/1968 | Edes. | |
| 3,547,121 | 12/1970 | Cherry. | |
| 3,668,394 | 6/1972 | Panzer. | |
| 3,835,992 | 9/1974 | Adamd, IV. | |
| 3,913,561 | 10/1975 | Maeda. | |
| 4,060,168 | 11/1977 | Romagnoli. | |
| 4,127,774 | 11/1978 | Gillen. | |
| 4,165,807 | 8/1979 | Yagi. | |
| 4,181,859 | 1/1980 | Vitalini. | |
| 4,274,006 | 6/1981 | Caine. | |
| 4,317,852 | 3/1982 | Ogden | 40/299 |
| 4,339,035 | 7/1982 | Marcus et al.. | |
| 4,426,783 | 1/1984 | Gerber et al.. | |
| 4,506,676 | 3/1985 | Duska. | |
| 4,735,194 | 4/1988 | Stiegmann. | |
| 4,754,750 | 7/1988 | Imonti | 602/58 |
| 4,764,948 | 8/1988 | Hurwitz. | |
| 4,813,062 | 3/1989 | Gilpatrick. | |
| 4,824,702 | 4/1989 | Straub | 428/40.1 |
| 4,860,331 | 8/1989 | Williams et al.. | |
| 4,985,019 | 1/1991 | Michelson. | |
| 5,232,452 | 8/1993 | Russell et al.. | |
| 5,309,840 | 5/1994 | Takamura et al.. | |
| 5,383,233 | 1/1995 | Russell. | |

FOREIGN PATENT DOCUMENTS

| | | | |
|---|---|---|---|
| 8972 | 2/1905 | United Kingdom | D24/189 |

OTHER PUBLICATIONS

1995 Brochure of Beekley Disposable Spots®.

*Primary Examiner*—Daniel W. Howell
*Assistant Examiner*—Gregory Andoll
*Attorney, Agent, or Firm*—Chilton, Alix & Van Kirk

[57] ABSTRACT

Disclosed herein is a radiographic marker system which includes a radiopaque marker mounted on a thin, flexible adhesive label. In one embodiment, the adhesive label has a central portion, the adhesive side of which is covered by a cut-out portion of the base tape to provide for comfortable removal of the marker after use. In another embodiment, the adhesive label has a gripping tab to facilitate removal from a base tape upon which the marker is supported before use, and to facilitate removal from a patient after use. The gripping tab is formed by a projecting tab of the label combined with a cut-out portion of the base tape which covers adhesive on the projecting tab. A method of making a radiology marker system according to the invention also is disclosed.

22 Claims, 2 Drawing Sheets

RADIOGRAPHIC MARKER SYSTEM AND METHOD OF MAKING SAME

BACKGROUND OF THE INVENTION

The present invention generally relates to medical imaging, and more particularly relates to radiographic markers for use in medical imaging.

Radiographic markers are used to designate high density areas of tissue or trauma sites on a patient prior to imaging. For example, radiographic markers are commonly used as nipple markers for chest x-rays and mammograms. A typical marker system includes a radiopaque marker, such as an arrow, letter, wire or "BB," which is mounted on an adhesive label. The adhesive label is stored on and supported by a wax-coated base tape prior to use. The adhesive label with the marker mounted thereon is removed from the base tape, applied to a patient prior to imaging, removed from the patient after imaging, and discarded.

Commercially available radiographic marker systems have several disadvantages. First, the labels of many of the known marker systems are made of very thin, flexible plastic and therefore it may be difficult to remove them from the base tape prior to use. Second, use of such labels may be inconvenient because the labels tend to stick to the user's hand during application. Third, when the labels are provided with a strong adhesive on the entire perimeter of their bottom surface in order that they remain firmly in place during use, it may be difficult to remove them from the patient's body after imaging. Fourth, because the labels typically have adhesive on the central portion of their surface, removal of the marker systems can be somewhat uncomfortable for the patient, particularly when used as nipple markers. It would be useful to develop a radiographic marker system which overcomes the above-mentioned problems while providing firm adhesion to a patient's body during use.

SUMMARY OF THE INVENTION

An object of the invention is to provide a convenient and effective marker system for use in medical imaging.

Another object of the invention is to provide a radiographic marker system having adhesive labels which will remain firmly in place during use and which can be easily and conveniently removed from a patient's body after imaging.

Another object of the invention is to provide a marker system in which the labels can be removed from a supporting base tape quickly and easily.

Yet another object of the invention is to provide a nipple marker system in which removal of the markers is not uncomfortable for the patient.

A further object of the invention is to provide a disposable radiographic marker system which is relatively inexpensive to manufacture.

Other objects of the invention will be in part obvious and in part pointed out more in detail hereinafter.

The invention in a preferred form is a radiographic marker system comprising a radiopaque marker, a label, and a base tape for supporting the label. The label has a front side for supporting the radiopaque marker and an opposite adhesive side, and includes a central portion and an extension portion extending outwardly from the central portion. A base tape is adhered to the adhesive side of the label. The base tape has a first cut-out portion underlying the central portion. The first cut-out portion is separable from the remainder of the base tape and is configured to remain adhered to the label when the label is removed from the base tape.

In a particularly preferred form of the invention, the label further includes a projecting tab projecting from the extension portion, and the base tape further includes a second cut-out portion underlying the projecting tab. The second cut-out portion is separable from the remainder of the base tape and is configured to remain adhered to the label when the label is removed from the base tape.

The label generally is thin and is formed from a flexible material such as paper or plastic. The base tape preferably has greater rigidity than the label. Thus, the first cut-out portion of the base tape imparts increased stiffness to the first projecting tab.

In one embodiment of the invention, the central portion of the label is round and the extension portions extend radially therefrom. Preferably, the first and second support arms have a width which is smaller than the diameter of the round central portion. In one particularly preferred embodiment of the invention, the label has a dumbbell-type configuration. In another particularly preferred form of the invention, the label has an hourglass-type configuration.

Another preferred form of the invention is a radiographic marker system comprising a radiopaque marker, a label, and a base tape for supporting the label. The label has a front side for supporting the radiopaque marker and an opposite adhesive side. The label includes a central portion and first and second support arms each having a length and extending outwardly from the central portion in generally opposite directions. At least one of the support arms has a projecting tab projecting therefrom. A base tape is adhered to the adhesive side of the label. The base tape has a primary cut-out portion underlying the projecting tab. The primary cut-out portion is separable from the remainder of the base tape and is configured to remain adhered to the label when the label is removed from the base tape. The projecting tab preferably extends outwardly from the support arm in a direction transverse to the length of the support arm. The projecting tab and primary cut-out portion preferably together form a gripping tab which is configured to be manually gripped by a user.

Yet another preferred form of the invention is a method of making a radiographic marker system. The method comprises the steps of obtaining a label which is removably mounted on a base tape, and obtaining a radiopaque marker. The label has a front side for supporting a radiopaque marker and an opposite adhesive side, and includes an extension portion extending outwardly from the central portion. The method further comprises the steps of mounting the radiopaque marker on the label, and forming a first cut-out portion in the base tape beneath the central portion of the label in order that the first cut-out portion becomes separated from the remainder of the base tape and remains in adhesive contact with the label when the label is removed from the base tape. In a particularly preferred form of the invention, the first cut-out portion of the base tape is formed by die cutting the base tape. The label preferably includes a projecting tab projecting from the central portion, and the method preferably further includes the step of forming a second cut-out portion in the base tape beneath the projecting tab in order that when the label is removed from the base tape the second cut-out portion is separated from the base tape and remains in contact with the label.

The invention accordingly comprises the several steps and the relation of one or more of such steps with respect to each of the others and the article possessing the features, properties, and the relation of elements exemplified in the following detailed disclosure.

DETAILED DESCRIPTION OF THE INVENTION

Figure 1:
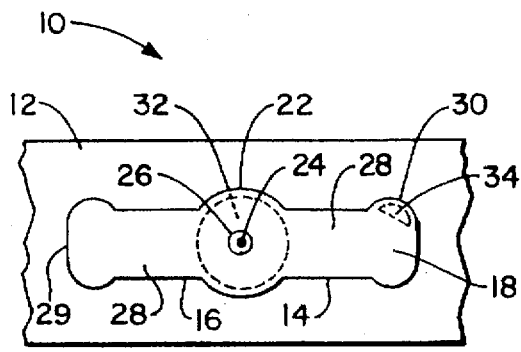
FIG. 1 shows the front side of a first embodiment of a radiographic marker system according to the present invention.
Figure 2:
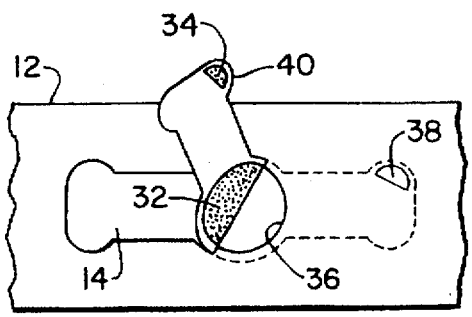
FIG. 2 shows the marker system of FIG. 1 with the label partially removed from the base tape.

Referring now to the drawings, and in particular to FIGS. 1–2, a radiographic marker system 10 is shown. The marker system 10 includes a base tape 12, which can be made of paper or another severable material, and can be coated with wax or any similar composition which allows for the release of the markers when they are to be placed on a patient. Base tape 12 is a single longitudinal strip.

A series of labels 14 each having an adhesive side 16 which contacts the base tape 12 and an opposite front side 18 are removably mounted in a row on the base tape 12. One such label is shown in FIGS. 1–2. The labels 14 can be made of any suitable thin, flexible material, and preferably are made of paper or plastic. A typical label 14 has a length of about 1½ inches and a width of ½–1 inch. The labels 14 have a central portion 22 which preferably, but not necessarily, is circular. In the middle of the central portion 22 a radiopaque marker 24, such as a "BB," shown in FIG. 1, an arrow, a letter, or another designation is mounted on the front side 18 of the label 14 using an adhesive 26 or any other suitable mounting means. The radiopaque marker 24 has a radiographic density sufficiently high to produce a discernable shadow on a radiographic image. The minimum density for the material of the radiopaque marker will depend upon the radiation intensity to which the marker will be subjected as well as the nature of the background subject matter. Higher marker densities may be used when higher levels of radiation intensity are employed. As used herein, the term "radiopaque" includes not only high density markers, such as those made of lead, which has a density of 11.3 g/cc, lead alloys, but also intermediate and low density materials which are partially radiopaque and partially radiolucent. For example, for mammography and other types of low level diagnostic radiology, the marker preferably has a radiographic density of at least about 1.1 g/cc.

The labels 14 have at least two wing-like support arms 28 extending outwardly from the central portion 22. In the preferred embodiment of FIGS. 1–2, the support arms 28 are elongated, extend radially outward in opposite directions and are co-planar with the central portion 22 when the base tape 12 is in an unwound, flat configuration. In the embodiment of FIGS. 1–2, the width of the support arms 28 is somewhat smaller than the diameter of the central portion 22. It is important that the support arms 28 are dimensioned and configured to provide sufficient adhesive surface area to ensure that the marker will remain firmly adhered to the patient during use.

Each of the support arms 28 has a pair of projecting tabs 30 which project outwardly in directions generally transverse, preferably perpendicular, to the length of the support arms 28. The projecting tabs 30 are in the plane of the support arms 28 when the base tape is in an unwound, flat configuration. The projecting tabs 30, which are further described below, are at the outer ends 29 of the support arms 28, and give the label a dumbbell-type configuration. The projecting tabs 30 are continuous with the support arms 28.

The adhesive side 16 of the support arms 28 is configured to be adhered to a patient to provide for a relatively firm hold of the label on the patient during imaging. Beneath the central portion 22 of the label 14, the base tape 12 is die cut in a circular shape having a size slightly smaller than the outer diameter of the central portion 22, forming a first or center cut-out portion 32. This center cut-out portion 32 of the base tape is coaxial with the central portion 22 and is designed to remain adhered to the adhesive side 16 of the label 14 when the label 14 is removed from the base tape 12. When the marker is placed upon the patient, the center cut-out portion 32 prevents the central portion 22 from adhering to the patient's body, thereby providing for improved comfort when the label is removed.

The base tape 12 also has a second cut-out portion 34 underlying one of the projecting tabs 30 of the label 14. The cut-out portion 34 preferably, but not necessarily, is generally D-shaped or oval-shaped, and can be die cut from the base tape 12. The curved portion of the D-shape conforms generally with the outer perimeter of the projecting tab 30. The peripheral cut-out portion 34 remains adhered to the label 14 when the label 14 is removed from the base tape 12. The second cut-out portion 34 in conjunction with the overlying projecting tab 30 together form a gripping tab 40 which is configured to be gripped between the thumb and forefinger of a user. More specifically, the gripping tab 40 imparts excellent gripability to the label 14 by enabling the user of the label to conveniently remove the labels manually from the base tape via the gripping tab 40 without requiring the use of a fingernail or other sharp instrument to "peel" the label off of the base tape 12. Simple and quick removal of the label 14 from the base tape 12 is thereby permitted. Furthermore, when holding the gripping tab 40, the user's finger does not stick to the back of the label 14, and thus the user can release the label 14 easily when the label 14 has been correctly positioned on a patient. The gripping tab 40 also provides for easy and convenient removal of the labels 14 from the patient after imaging because the gripping tabs 40 are not adhered to the patient's body.

As shown in FIG. 2, when the label 14 is removed from the base tape 12, center cut-out portion 32 and second cut-out portion 34 of the base tape 12 remain adhered to the label when the label is removed from the remainder of the base tape 12. As a result, where the label 14 has been separated from the base tape 12, the base tape has a circular opening 36 and a small D-shaped opening 38 where the cut-out portions 32, 34 of the base tape 12 were removed with the label 14.

In an alternate embodiment of the marker (which is not separately illustrated) the projecting tab has no adhesive thereon. In this embodiment the adhesive is selectively applied to the adhesive side of the label by spot adhesion, and no adhesive is applied to the projecting tab. As a result, there is no cut-out portion connected to the projecting tab when the label is removed from the base tape.

The marker system 10 is made in the following manner. A dual layer strip including an elongated strip of the base tape 12 having a wax coating on one side thereof and an elongated, continuous strip of plastic label material removably adhered thereto is obtained in the form of a roll. The dual layer strip is mounted on a converting machine and the label material is printed with any indicia to be included on the labels 14 when the roll is in a partially unrolled condition. The labels 14 are then die cut from the upper side of the dual layer strip and the base tape 12 is die cut from the bottom side of the unrolled dual layer strip. Before or after die cutting, adhesive for a radiographic marker is placed on the exposed side of the label material, a radiographic marker is positioned on the adhesive, and the adhesive is cured. After curing the marker system 10 is rolled and packaged.

Figure 3:
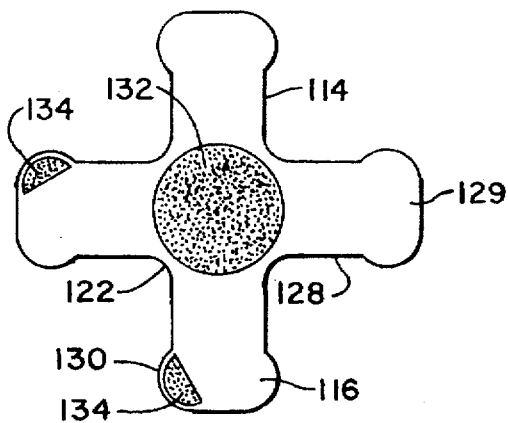
FIG. 3 is an enlarged view of the adhesive side of a second embodiment of a radiographic marker according to the invention after removal from the base tape.

A label for a second embodiment of a radiographic marker system is shown in an enlarged view in FIG. 3 and is designated as 114. This label 114, which is shown from the adhesive side 116 after removal from a base tape, has four support arms 128 extending at right angles to each other. Each support arm 128 has a pair of projecting tabs 130 extending outwardly from the outer end 129 of the support arm 128 in opposite directions perpendicular to the support arm 128. This embodiment of the label, as well as the embodiments shown in FIGS. 4–6, provide for even more stable placement of the label on a patient, and are particularly useful on large, protruding nipples or when the marker is to be placed on a part of the patient's body which will be subjected to angular movement, such as a finger joint or elbow.

In the embodiment of FIG. 3, the base tape (not shown) is die cut beneath the central portion 122 of the label 114 in a circular shape, forming a center cut-out portion 132. The central portion 122 of the label 114 is of a square shape and the length of a side of the square is equal to the width of the support arms 128. The center cut-out portion 132 of the base tape 112 prevents the central portion 122 of the label 114 from adhering to a patient's body. The base tape has two peripheral cut-out portions 134 which are adhered to projecting tabs 130 which extend from separate and adjacent support arms 128 of the label 114.

Figure 4:
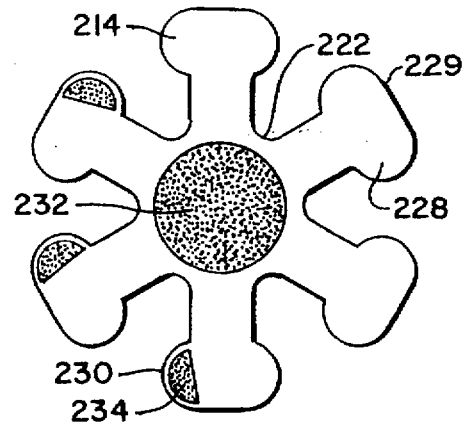
FIG. 4 is an enlarged view of the adhesive side of a third embodiment of a radiographic marker according to the invention after removal from the base tape.

FIG. 4 shows an enlarged view of the adhesive side of a third embodiment of a label for a radiographic marker according to the invention, designated as 214. The label 214, which has been removed from a base tape, has a hexagonal central portion 222 with six support arms 228 extending outwardly therefrom, each of which has a pair of oppositely extending projecting tabs 230 at the outer end 229 thereof. A center cut-out portion 232 of base tape material having a circular shape is adhered to the central portion 222. Three projecting tabs 230 on adjacent support arms 228 have peripheral cut-out portions 234 of a base tape adhered thereto.

Figure 5:
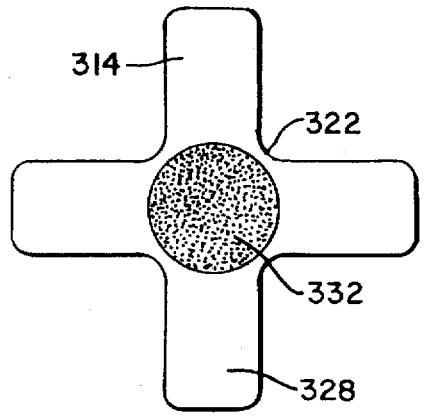
FIG. 5 is an enlarged view of the adhesive side of a fourth embodiment of a radiographic marker according to the invention after removal from the base tape.
Figure 6:
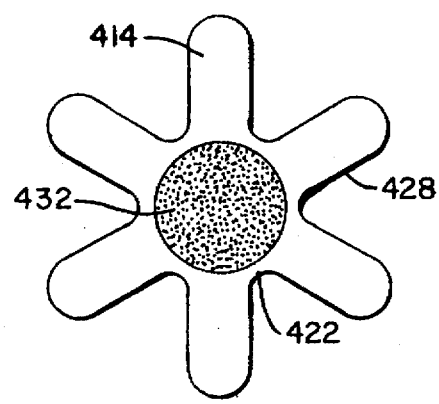
FIG. 6 is an enlarged view of the adhesive side of a fifth embodiment of a radiographic marker according to the invention after removal from the base tape.

A fourth embodiment of a label for the marker system of the invention is shown in an enlarged view in FIG. 5, with the adhesive side facing forward. The label, which is designated as 314, has been removed from a base tape. This embodiment has a square central portion 322 with four radially extending support arms 328, none of which have projecting tabs. This embodiment has a circular center cut-out portion 332 adhered to the central portion 322, but does not have any second cut-out portions, and therefore has no gripping tabs.

A fifth embodiment of a label for the marker system of the invention is shown in FIG. 6. This embodiment, which is designated as 414, has a hexagonal central portion 422 with six radially extending support arms 428, none of which have projecting tabs. This embodiment has a circular center cut-out portion 432 below the central portion 422, but does not have any peripheral cut-out portions, and therefore has no projecting tabs.

Figure 7:
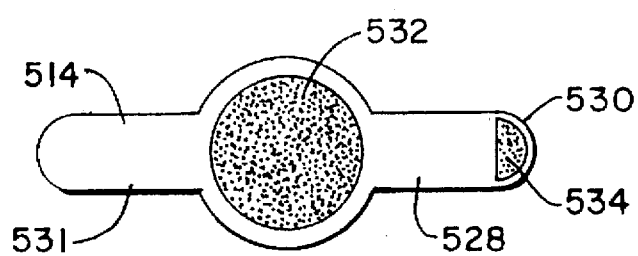
FIG. 7 is an enlarged view of the adhesive side of a sixth embodiment of a radiographic marker according to the invention after removal from the base tape.

A sixth embodiment of a label for the marker system of the invention is shown in FIG. 7 and is designated as 514. This embodiment, which is shown with the adhesive side up and the base tape removed, is similar to that of FIGS. 1–2 with the exception that projecting tab 530 extends outwardly from a short support arm 528 in a direction that is parallel, rather than perpendicular, to the support arm 528. The other support arm 531 is equivalent in length to the combination of support arm 528 and projecting tab 530. The projecting tab 530 has a D-shaped peripheral cut-out portion 534 adhered thereto. A center cut-out portion 532 is adhered to a central portion 522 of the label 514. This embodiment of the label has a smaller amount of surface area to be adhered to the patient than the embodiments shown in FIGS. 1–6.

Figure 8:
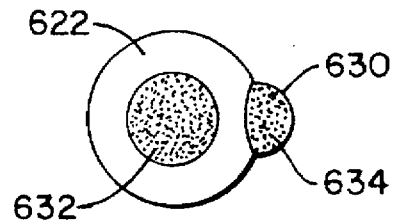
FIG. 8 is an enlarged view of the adhesive side of a seventh embodiment of a radiographic marker according to the invention after removal from the base tape.

A seventh embodiment of a label for the marker system of the invention is shown in FIG. 8. This embodiment, which is shown with the adhesive side up and the base tape removed, has a round central portion 622 with a single coplanar projecting tab 630 projecting outwardly therefrom. The projecting tab has a length which is equal to about ⅓ of the diameter of the central portion 622 and a width which is equal to about ¼ of the diameter of the central portion 622. The projecting tab 630 has a peripheral cut-out portion 634 adhered thereto and a center cut-out portion 632 adhered to the middle of the central portion 622.

Figure 9:
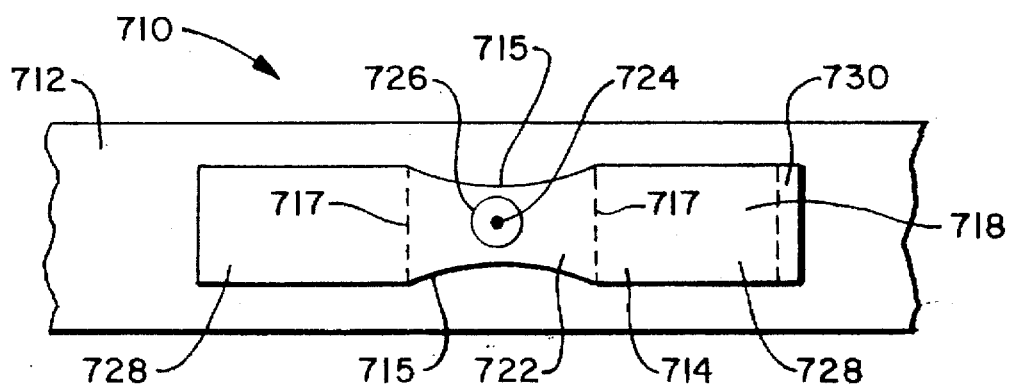
FIG. 9 is an enlarged view of the front side of an eighth embodiment of a radiographic marker system according to the invention.
Figure 10:
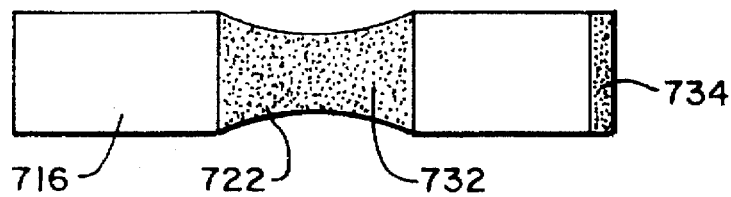
FIG. 10 is an enlarged view of the adhesive side of the radiographic marker for the system of FIG. 9 after removal from the base tape.

An eighth embodiment of a label for the marker system of the invention is shown in FIGS. 9–10. As shown in FIG. 9, the marker system 710 includes a base tape 712 with a series of hourglass-shaped labels, one of which is shown and is designated as 714, removably mounted thereon. A radiopaque marker 724 is mounted on the front side 718 of the label 714 with an adhesive 726. This embodiment is shown with the adhesive side up and the base tape removed. The label 714 includes a central portion 722 having a pair of support arms 728 extending outwardly therefrom in opposite directions. The central portion 722 has a pair of opposite curved sides 715 which taper inwardly at the center and outwardly toward the ends, and a pair of straight sides 717. The support arms 728 are generally rectangular and extend from the straight sides 717 of the central portion 722 in a continuous manner. In the embodiment of FIGS. 9–10, the width of the support arms 728 is equivalent to the length of the straight sides 717, and the length of support arms 728 is generally the same as the length of the central portion 722. This configuration of the label is particularly preferred when a large amount of adhesive surface area, provided by the support arms 728, is required. The support arms 728 are dimensioned and configured to provide even greater adhesive surface area than the support arms of the embodiment shown in FIGS. 1–2 to provide for secure adhesion to a patient during use. A rectangular projecting tab 730 having a length which is equivalent to the width of the support arms 728 extends along the outer side of one of the support arms 728.

The label 714 has an adhesive side 716, which is shown in FIG. 10. The base tape 712 is die cut such that a center cut-out portion 732 underlying the central portion 722 (but shown on top in FIG. 10) and having the same shape as the central portion 722 remains adhered to the label 714 when the label 714 is removed from the base tape 712. The center cut-out portion 732 prevents the central portion 722 of the label from adhering to the patient during use, thereby providing for comfortable removal of the label 714 after use.

A second cut-out portion 734 underlies the projecting tab 730. The second cut-out portion 734 together with the projecting tab 730 form a gripping tab which is configured to be manually held during removal of the label 714 from the base tape 712 and during removal of the label 714 from the patient after use. The second cut-out portion 734 thus remains adhered to the label 714 when the label 714 is used.

As will be apparent to persons skilled in the art, various modifications and adaptations of the structure above described will become readily apparent without departure from the spirit and scope of the invention, the scope of which is defined in the appended claims.

What is claimed is:

1. A radiographic marker system, comprising:
   a radiopaque marker,
   a label having a front side for supporting the radiopaque marker and an opposite adhesive side, the label including a central portion and an extension portion extending outwardly from the central portion, and
   a base tape adhered to the adhesive side of the label, the base tape having a first cut-out portion underlying the central portion, the first cut-out portion being separable from the remainder of the base tape and being configured to remain adhered to the label when the label is removed from the base tape.

2. A radiographic marker system according to claim 1, wherein the label further includes a projecting tab projecting from the extension portion, and the base tape further includes a second cut-out portion underlying the projecting tab, the second cut-out portion being separable from the remainder of the base tape and being configured to remain adhered to the label when the label is removed from the base tape.

3. A radiographic marker system according to claim 2, wherein the second cut-out portion imparts increased stiffness to the projecting tab.

4. A radiographic marker system according to claim 1, wherein the extension portion includes first and second support arms extending outwardly from the central portion.

5. A radiographic marker system according to claim 4, wherein the central portion of the label has a diameter and the support arms have a width which is smaller than the diameter of the central portion.

6. A radiographic marker system according to claim 4, wherein the label has a dumbbell-type configuration.

7. A radiographic marker system according to claim 4, wherein the extension portion includes third and fourth support arms extending outwardly from the central portion.

8. A radiographic marker system according to claim 7, wherein the extension portion further includes fifth and sixth support arms extending outwardly from the central portion.

9. A radiographic marker system according to claim 1, wherein the label has an hourglass-type configuration.

10. A radiographic marker system, comprising:
    a radiopaque marker,
    a label having a front side for supporting the radiopaque marker and an opposite adhesive side, the label having a central portion and first and second support arms each having a length and extending outwardly from the central portion in generally opposite directions, at least one of the support arms having a projecting tab projecting therefrom, and
    a base tape adhered to the adhesive side of the label, the base tape having a primary cut-out portion underlying the projecting tab, the second cut-out portion being separable from the remainder of the base tape and being configured to remain adhered to the label when the label is removed from the base tape.

11. A radiographic marker system according to claim 10, wherein the projecting tab and primary cut-out portion together form a gripping tab which is configured to be manually gripped by a user.

12. A radiographic marker system according to claim 10, wherein the base tape has a secondary cut-out portion underlying the central portion, the first cut-out portion being separable from the remainder of the base tape and being configured to remain adhered to the label when the label is removed from the base tape.

13. A radiographic marker system according to claim 12, wherein the projecting tab and primary cut-out portion together form a gripping tab which is configured to be manually gripped by a user.

14. A radiographic marker system according to claim 10, wherein the label has a dumbbell-type configuration.

15. A radiographic marker system according to claim 12, wherein the label has a dumbbell-type configuration.

16. A radiographic marker system according to claim 10, wherein the label further includes third and fourth support arms extending outwardly from the central portion.

17. A radiographic marker system according to claim 12, wherein the label has an hourglass-type configuration.

18. A method of making a radiographic marker system comprising:
    obtaining a label having a front side for supporting a radiopaque marker and an opposite adhesive side, the label including a central portion and an extension portion extending outwardly from the central portion, the adhesive side of the label being removably mounted on a base tape,
    obtaining a radiopaque marker,
    mounting the radiopaque marker on the label, and
    forming a first cut-out portion in the base tape beneath the central portion of the label in order that when the label is removed from the base tape the first cut-out portion is separated from the remainder of the base tape and remains in contact with the label.

19. A method according to claim 18, wherein the first cut-out portion is formed by die cutting the base tape.

20. A method according to claim 18, wherein the label has a projecting tab projecting from the extension portion, and the method further includes the step of:
    forming a second cut-out portion in the base tape beneath the projecting tab in order that when the label is removed from the base tape the second cut-out portion is separated from the remainder of the base tape and remains in contact with the label.

21. A method according to claim 20, wherein the base tape has a greater rigidity than the label and the second cut-out portion of the base tape imparts increased stiffness to the projecting tab.

22. A method according to claim 18, wherein the label has a dumbbell-type configuration.

* * * * *

UNITED STATES PATENT AND TRADEMARK OFFICE
CERTIFICATE OF CORRECTION

PATENT NO. : 5,702,128
DATED : Dec. 30, 1997
INVENTOR(S) : Maxim et al

It is certified that error appears in the above-identified patent and that said Letters Patent is hereby corrected as shown below:

Column 8, line 10, delete "second" and replace with

-- primary --.

Column 8, line 19, delete "first" and replace with

-- secondary --.

Signed and Sealed this

Twenty-eighth Day of July, 1998

Attest:

BRUCE LEHMAN

*Attesting Officer*     *Commissioner of Patents and Trademarks*